United States Patent [19]

Mlot-Fijalkowski

[11] 4,331,027
[45] May 25, 1982

[54] DUAL-PURPOSE PENETRANT SYSTEM

[75] Inventor: Adolf Mlot-Fijalkowski, Lincolnwood, Ill.

[73] Assignee: Magnaflux Corporation, Chicago, Ill.

[21] Appl. No.: 137,629

[22] Filed: Apr. 7, 1980

[51] Int. Cl.³ ............................................. G01B 11/30
[52] U.S. Cl. ...................................................... 73/104
[58] Field of Search ................................. 73/104, 105; 252/301.19, 408

[56] References Cited

U.S. PATENT DOCUMENTS 3,028,338  4/1962  Parker et al. .......................... 73/104
3,557,015  1/1971  Alburger .......................... 252/301.19

Primary Examiner—Donald O. Woodiel
Attorney, Agent, or Firm—Hill, Van Santen, Steadman, Chiara & Simpson

[57] ABSTRACT

Method and composition for detecting flaws in a workpiece utilizing either white light or ultraviolet light wherein a penetrant solution is applied to the surface of the workpiece, the penetrant solution containing a rhodamine dye dissolved in a solvent, the dye possessing an inherent color and being capable of fluorescing under the influence of ultraviolet light. The excess penetrant is removed from the surface in accordance with usual practice, while leaving penetrant entrapped in any surface flaws. An improved developer is applied to the surface, the developer consisting of a suspension including a finely divided developer powder suspended in the same dye solvent as in the penetrant in a sufficient amount to lower the concentration of rhodamine dye in the entrapped penetrant below that at which quenching of fluorescence occurs. The indications thus produced under both visible light and ultraviolet light are distinct and non-blurring, enabling the piece to be inspected under either type of light source.

5 Claims, No Drawings

DUAL-PURPOSE PENETRANT SYSTEM

BACKGROUND OF THE INVENTION

1. Field of the Invention

The present invention is in the field of nondestructive testing by the penetrant inspection method and provides a dual purpose penetrant and dual purpose developer enabling the system to be used under either white light excitation or excitation by ultraviolet light.

2. Description of the Prior Art

There have been some disclosures of dual purpose penetrant systems for some time. Generally, the compositions employed in such systems are based either on a single fluorescent dye in combination with one or more cascading agents.

For example, when using the system described in U.S. Pat. No. 3,028,338, the developed indications are reasonably deep in visible color and compare favorably with standard visible dye indications. However, the fluorescent counterparts are essentially void of brilliance and the indications are not nearly as good as those obtained with conventional fluorescent systems on the market. It is believed that the reduced intensity fluorescent indications are due to a phenomenon known as fluorescent quenching which usually occurs when the concentration of the fluorescent material exceeds a predetermined value.

A different approach to dual purpose penetrant systems has been employed in U.S. Pat. No. 3,557,015. In this patent is described a system in which a non-fluorescent dye is combined with a fluorescent dye and used simultaneously in the penetrant to provide two different levels of sensitivity. The theory is that the visible non-fluorescent dyes are better able to detect large surface cracks while the fluorescent dyes are more useful in connection with the very fine surface cracks.

SUMMARY OF THE INVENTION

The present invention provides a dual purpose penetrant system which utilizes only a single dye material in the penetrant but nevertheless provides a useful combination of penetrant and developer suitable for inspection under white light or under ultraviolet light without the necessity of adding any cascading additives or using two different types of dyes. Specifically, in the present invention a rhodamine dye which has a characteristic visible color and which is capable of fluorescing under ultraviolet light is incorporated into the penetrant in solution in a suitable solvent which most preferably is benzyl alcohol. The penetrant vehicle is either removable by water or by organic solvents, depending upon the other materials contained therein. The penetrant is used in the usual penetrant inspection process, by application to the surface of the test piece with a sufficient dwell time being permitted to enable the penetrant to find its way into surface flaws, and into subsurface flaws which have an opening at the surface. The excess penetrant is then removed in the usual manner by means of a water wash if the penetrant vehicle is water removable, or by means of an organic solvent if the penetrant is not water washable. An improved developer is then added to aid in bringing the entrapped penetrant back to the surface where it is rendered visible to its background. The developer includes finely divided inert particles suspended in a liquid vehicle which includes the same type of solvent as used in the penetrant. In the preferred form of the invention, the developer contains benzyl alcohol which is capable of diluting relative concentration of the rhodamine dye in the entrapped deposits and thereby eliminating the quenching effect which has heretofore been troublesome in dual penetrant inspection systems. The inspection may then be carried out under ordinary white light or under ultraviolet light to determine the location and extent of flaws which have been located by the entrapped penetrant.

DESCRIPTION OF THE PREFERRED EMBODIMENTS

The penetrant composition of the present invention is based upon the use of a fluorescent dye of the rhodamine type. This fluorescent dye can be "Calco Rhodamine Base DY" which has the same Colour Index number as Rhodamine B, Rhodamine 6G and Rhodamine 6GON, both of which have Colour Index numbers of 45,160. These materials, beside being fluorescent, have fairly intense visible colors so that they yield usable indications in white light. For the purposes of the present invention, the penetrant should contain from about 1 to 10% by weight of the rhodamine dye.

The solvent present in the penetrant solution is instrumental in securing the improved results. The solvent preferred for overall use in accordance with the present invention is benzyl alcohol. Other oxygen containing organic solvents can be used such as acetone, isopropanol, hexanol, n-butyl alcohol, tridecyl alcohol, phenyl methyl carbinol, and ethoxylated alcohol surfactants. Some of these solvents are too volatile to be useful for extended periods of time. Others are not as effective as benzyl alcohol because they cause excessive bleeding. Still others present problems of toxicity or corrosiveness.

The following formulation has been found to be a satisfactory base for penetrant compositions according to the present invention:

| | |
|---|---|
| Benzyl Alcohol | 60 parts by weight |
| "Ninol 201" (alkylolamides) | 20 parts by weight |
| Calco Rhodamine Base DY | Up to 9.5 parts by weight |

These formulations can be made either water or solvent removable. The presence of the benzyl alcohol and the alkylolamide which is added for better wetting properties makes the formulations easily compatible with aromatic solvents which also lower the material cost. The most effective penetrant used thus far is as follows:

| | |
|---|---|
| Benzyl Alcohol | 55 parts by weight |
| "Ninol 201" | 20 parts by weight |
| "Ninol 1281" | 5 parts by weight |
| Calco Rhodamine Base DY | 4 parts by weight |

The "Ninol 1281" is another type of alkylolamide which is added as a corrosion inhibitor. Both the "Ninols" are excellent solvents for the dye as well as contributing to the quality of the penetrant's fluorescence.

It is also possible to use some ethoxylated surfactants in place of the two types of alkylolamides referred to previously. For example, "Tergitol 15-S-5" or "Surfonic N-60" were both found to be suitable because of their limited water removal characteristics.

Turning to the developer composition, the developer should contain non-liquid developing constituents which limit bleeding to retain the sharpness of the indications with time. To produce a good visible indication, more bleedout is required than is required to produce a good fluorescent indication. If there is too much bleedout, the fluorescent indications become blurry. By carefully selecting the constituents which limit the bleeding but still increase contrast, a balance can be achieved between the two systems.

Insofar as the developer solvent is concerned, I include a relatively non-volatile solvent having good solvency toward rhodamine dyes in combination with one or more volatile solvents. Such volatile solvents may be ethanol-acetone, ethanol-ethyl acetate, or methylene chloride when non-flammability is important.

The solvent should be present in the developer system to the extent of from 0.5 to 15% by weight, exclusive of volatile solvents. In other words, the developer composition remaining after evaporation of the relatively volatile solvents should contain about 0.5 to 15% by weight of the solvent for the dye in the penetrant.

The following formulation provided an effective dual range developer which is free of chlorine:

| | |
|---|---|
| "Tullanox 292" (silica aerogel) | 2.06% by weight |
| Pentaerythritol (powdered) | 12.37% by weight |
| "Carbowax 4000" (polyethylene glycol) | 1.03% by weight |
| "Plurafac D-25" (ethoxylated fatty alcohols) | 1.03% by weight |
| Benzyl alcohol | 1.03% by weight |
| Ethanol | 20.61% by weight |
| Ethyl acetate | 61.85% by weight |

After evaporation of the ethanol and ethyl acetate, the developer composition was as follows:

| | |
|---|---|
| "Tullanox 292" | 11.75% by weight |
| Pentaerythritol | 70.60% by weight |
| "Carbowax 4000" | 5.88% by weight |
| "Plurafac D-25" | 5.88% by weight |
| Benzyl alcohol | 5.88% by weight |

The following developer formulation was designed for use where the developer must be non-flammable:

| | |
|---|---|
| "Tullanox 292" | 1.27% by weight |
| Pentaerythritol | 7.64% by weight |
| "Carbowax 4000" | 0.63% by weight |
| "Plurafac D-25" | 0.63% by weight |
| Benzyl alcohol | 0.63% by weight |
| 1-1-1 trichloroethane | 25.47% by weight |
| Methylene chloride | 63.69% by weight |

The residue after evaporation of the volatile solvents was substantially the same as that given for the previous composition.

In the compositions given above, the pentaerythritol functions as an additional developing agent. The polyethylene glycol is added as a thickener.

The specific developers set forth above both produced sharp visible red indications with a penetrant composition containing rhodamine dyes dissolved in benzyl alcohol. The indications did not become blurry with time as occasionally occurs with commercial visible penetrant systems. The two developers produced sharp orange fluorescent indications when examined under ultraviolet light.

It should be evident that various modifications can be made to the described embodiments without departing from the scope of the present invention.

I claim as my invention:

1. A method for detecting flaws in a workpiece under either white light or ultraviolet light which comprises the steps of:
    applying to the surface of said workpiece a penetrant solution containing a rhodamine dye dissolved in an oxygen containing organic solvent, said dye possessing an inherent color and being capable of fluorescing under the influence of ultraviolet light, removing excess penetrant from said surface while leaving penetrant entrapped in any surface flaws, and
    applying a developer suspension to the surface, said developer suspension including a finely divided developer powder and the same dye solvent as in said penetrant in a sufficient amount to lower the concentration of rhodamine dye in the entrapped penetrant below that at which quenching of fluorescence occurs.

2. A method according to claim 1 in which said penetrant contains from 1 to 10% by weight of said rhodamine dye.

3. A method according to claim 1 in which said solvent is benzyl alcohol.

4. A method according to claim 1 in which the solvent in said developer constitutes from 0.5 to 15% by weight of said developer, exclusive of volatile solvents.

5. A method according to claim 1 in which:
    said penetrant also includes a wetting agent.

* * * * *